US008206405B2

(12) United States Patent
Beverland et al.

(10) Patent No.: US 8,206,405 B2
(45) Date of Patent: Jun. 26, 2012

(54) ACETABULAR CUP POSITIONING

(75) Inventors: David Beverland, Holywood (GB); Alec Paul Birkbeck, Leeds (GB); Frank Foley, Dorset (GB); Ian Revie, Boroughbridge (GB); Mike Slomczykowski, Leeds (GB)

(73) Assignee: Depuy International Limited (GB)

( * ) Notice: Subject to any disclaimer, the term of this patent is extended or adjusted under 35 U.S.C. 154(b) by 1041 days.

(21) Appl. No.: 11/869,381

(22) Filed: Oct. 9, 2007

(65) Prior Publication Data
US 2008/0255584 A1  Oct. 16, 2008

(30) Foreign Application Priority Data

Apr. 9, 2005 (GB) .................................. 0507243.4
Apr. 6, 2006 (WO) ................ PCT/GB2006/001275

(51) Int. Cl.
*A61B 1/00* (2006.01)
*A61B 1/04* (2006.01)
(52) U.S. Cl. ....................................... 606/130; 606/102
(58) Field of Classification Search .................... 606/91, 606/130, 102; 703/11; 623/22.21
See application file for complete search history.

(56) References Cited

U.S. PATENT DOCUMENTS

| 5,007,936 | A | 4/1991 | Woolsen |
| 6,395,005 | B1 | 5/2002 | Lovell |
| 2002/0077540 | A1* | 6/2002 | Kienzle, III .................. 600/424 |
| 2004/0117029 | A1* | 6/2004 | Lewis et al. ................. 623/22.28 |
| 2005/0021043 | A1 | 1/2005 | Jansen |
| 2005/0065617 | A1* | 3/2005 | Moctezuma de la Barrera et al. ............................ 623/908 |

FOREIGN PATENT DOCUMENTS

| EP | 1406203 A2 | 4/2004 |
| EP | 1406203 A | 4/2007 |
| WO | WO 2004084740 A1 | 10/2004 |

OTHER PUBLICATIONS

International Search Report and Written Opinion, dated 14 Jun. 2006, 18 pages.
PCT Request, 4 pages.
JP2008-504846 Notification with refs cited dated Jan. 4, 2011.

* cited by examiner

*Primary Examiner* — Thomas C. Barrett
*Assistant Examiner* — Christian Sevilla (57) ABSTRACT

A computer aided surgery system, method, surgical method and instrument for guiding the positioning of an acetabular cup in a pelvis are described. The position of the transverse acetabular ligament of the pelvis and the position of the acetabular labrum of the pelvis are determined. The orientation of an acetabular plane including the acetabular labrum and the transverse acetabular ligament is calculated. A planned position for the acetabular cup is determined, in which an inlet plane of the cup is substantially parallel to the acetabular plane. The instrument comprises a mounting for attaching the instrument to a patient, a support, a guide defining a longitudinal axis, and for receiving a further instrument bearing the acetabular cup implant, and an adjustment mechanism. The adjustment mechanism can allow the angular orientation of the guide to be adjusted about at least two different axes to allow the inclination and version or anteversion of the longitudinal axis to be altered.

8 Claims, 7 Drawing Sheets

ACETABULAR CUP POSITIONING

The present invention relates to positioning an acetabular cup, and in particular to determining the position and orientation for implanting an acetabular cup in the acetabulum for a prosthetic hip.

One approach to hip replacement surgery is to use an acetabular cup which is located within the acetabulum of the pelvis. The acetabular cup provides a prosthetic articulating surface against which an articulating surface of the femoral head, or a prosthetic femoral head, can bear in use. There are a number of factors to consider in correctly locating an acetabular cup so as to ensure that the replacement prosthetic joint replicates the natural joint as closely as possible. These include the position of the cup within the acetabulum, and also the angular orientation of the acetabular cup in the acetabulum. There is therefore a complex interplay between both the position and orientation of the acetabular cup and the resulting performance of the prosthetic joint.

The orientation of the plane of the mouth of an acetabular cup can be defined in terms of the angles between an axis of the acetabular cup and the cardinal anatomic planes of the pelvis, i.e. the saggital or medial plane, the coronal or frontal plane and the transverse plane. The abduction angle, or inclination, is measured between the transverse pelvic plane and the axis of the acetabular cup. An abduction angle in the range of about $40\text{-}50^E$ is generally recommended in practice, however, there is no clear definition of the acetabular cup axis used to define that angle. The version angle is measured between the frontal pelvic plane and an axis of the acetabular cup and is generally recommended in practice to be in the range of about $20\text{-}30^E$. However, again, there is no clear definition of the how the axis of the acetabular cup is defined. Therefore, although the are some generally accepted ranges of values for the abduction and version angles there is no precise definition of how to determine them relative to the cardinal planes of the pelvis.

Further, while the orientation of the mouth of the acetabular cup is generally defined with respect to the local planes of the pelvis, many alignment instruments and surgeons use the mid-saggital axis of the spine as an alignment axis.

There are other inconsistencies in current acetabular cup positioning strategies. Some strategies use the bony rim of the acetabulum as an alignment reference. However, while the rim of the acetabulum may define the structural inlet plane of the acetabulum, it does not necessarily define the functional inlet plane of the acetabulum. Further, the rim may also be deformed by the disease process and may therefore not be a reliable reference point.

The orientation of the acetabular cup can be varied throughout three-dimensional space and therefore at least two angles are required in order to uniquely specify its orientation. However, it is also necessary to have reliable reference or datum points from which to measure those angles. The main anatomical planes (saggital, coronal and transverse) of the entire body will be referred to as the global planes, whereas the same main anatomical planes of the pelvis will be referred to as the local planes.

The global and local planes are not necessarily coincident as the pelvis can move relative to the rest of the human body. The spatial relationship between the global and local planes is variable. For example, in anatomical text books, the lumbar-sacral angle is given as $30^E$ and the lumbar lordosis angle has a wide variation in the range of $30^E$ to $50^E$. Hence there is a significant variation in the angular relationship between the global and local planes. These planes cannot be identified using external landmarks and so accurate positioning of a patient for x-ray or surgery is difficult if not impossible.

Further, the healthy lumbar spine very mobile allowing up to $60^E$ of flexion, $35^E$ of extension and $20^E$ of lateral flexion and angular changes. While not all patients undergoing hip replacement surgery have totally mobile spines, to the extent they do, then this potential for movement of the pelvis relative to the body can further complicate the precise location of the local planes relative to the global planes.

Current intra-operative techniques derive local planes of the pelvis from x-rays of the pelvis with the patient on the operating table, together with a visual assessment of the location of the global planes of the patient. However, both of these are crude assessments and there is also the likelihood of the relationship changing during the surgical procedure if the patients pelvis moves.

Therefore current approaches are flawed both in terms of how the orientation of the acetabular cup is defined and also in terms of the subjective manner in which the correct orientation and position is achieved during surgery.

It would therefore be beneficial to be able to more reliably locate the acetabular cup within the acetabulum.

The present invention is based on aligning the acetabular cup based on the positions of the transverse acetabular ligament and/or the acetabular labrum. In this way, the acetabular cup is aligned more accurately with the functional acetabulum rather than physical acetabulum so as to more completely reproduce the original behaviour of the hip joint.

According to a first aspect of the present invention, there is provided a computer aided surgery system for guiding the positioning of an acetabular cup in a pelvis of a patient. The system can comprise a data processing device and a memory storing computer program instructions. The computer program instructions can configure the data processing device to: determine the position of the transverse acetabular ligament; determine the position of the acetabular labrum; calculate the orientation of an acetabular plane including the acetabular labrum and the transverse acetabular ligament; and determine a planned position for the acetabular cup. An inlet plane of the cup can be substantially parallel to the acetabular plane.

As the transverse acetabular ligament and acetabular labrum are used as local landmarks to determine the correct position for an acetabular cup implant, the computer aided surgery system allows the functional behaviour of the patient's hip joint to be more reliably reproduce. Further, this approach does not rely on having to determine the anatomical planes of the pelvis or the patient's body. Furthermore, this approach is patient specific as it depends on an individual patients anatomy rather than being based on a model or assumed behaviour.

The memory can further store computer program instructions for causing the data processing device to identify an acetabular cup template best matching the size of the acetabulum from acetabulum shape data representing the shape of the acetabulum. Hence, shape data can be used to automatically identify a cup template best matching the patients anatomy.

The memory can further store computer program instructions for causing the data processing device to display a visual indication of the orientation of the acetabular plane. This provides a visual cue which can be used by a surgeon to more accurately position an acetabular cup implant. Hence, an image guided surgery (IGS) system can be provided.

The memory can further store computer program instructions for causing the data processing device to determine the position of an acetabular cup template; and display a visual representation of the acetabular cup template. Hence, the surgeon or user can visually compare the template position and the intended position as defined by the acetabular plane.

The memory can further store computer program instructions for causing the data processing device to receive data to alter a stored planned position for the acetabular cup. Hence, the surgeon can manually alter the stored planned position so as to fine tune the position or to take into account any abnormalities in the particular surgical site.

The memory can further store computer program instructions for causing the data processing device to determine the current position of a reaming device and/or display a visual indication of the current position of the reaming device. Hence, a visual mechanism is provided for guiding reaming of the acetabular cavity by the surgeon.

The memory can further store computer program instructions for causing the data processing device to determine the current position of an acetabular cup implant and/or display a visual indication of the current position of the acetabular cup implant. Hence, a visual guide to assist in positioning the acetabular cup implant can be provided.

According to a further aspect of the invention, there is provided a computer aided surgery method for guiding the positioning of an acetabular cup in a pelvis of a patient. The method can comprise determining the position of at least a part of the transverse acetabular ligament; determining the position of at least a part of the acetabular labrum of the pelvis; calculating the orientation of an acetabular plane including the acetabular labrum and the transverse acetabular ligament; and determining a planned position for the acetabular cup. An inlet plane of the cup can be substantially parallel to the acetabular plane.

The computer aided surgery method has similar benefits to those provided by the computer aided surgery system.

The method can further comprise identifying an acetabular cup template best matching the size of the acetabulum from acetabulum shape data representing the shape of the acetabulum.

The method can further comprise displaying a visual indication of the orientation of the acetabular plane. This can facilitate the correct positioning of an acetabular cup implant.

The method can further comprise determining the position of an acetabular cup template; and displaying a visual representation of the acetabular cup template.

The method can further comprise receiving data to alter a stored planned position for the acetabular cup. In this way, a surgeon can manual change a planned position.

The method can further comprise determining the current position of a reaming device; and displaying a visual indication of the current position of the reaming device.

The method can further comprise determining the current position of an acetabular cup implant and/or displaying a visual indication of the current position of the acetabular cup implant.

According to a further aspect of the invention, there is provided a method for guiding the positioning of an acetabular cup in the pelvis of a patient. The method can comprise determining the orientation of an acetabular plane defined by the acetabular labrum and transverse acetabular ligament of the pelvis; and implanting the acetabular cup in the acetabulum of the pelvis with an inlet plane of the acetabular cup substantially parallel to the acetabular plane.

The can further comprise determining an acetabular cup template best matching the shape of the acetabulum.

The method can further comprise using the best matching acetabular cup template or implant to plan the position of the acetabular cup implant.

The acetabular cup can be implanted at a position at which the inlet plane is located medial of the acetabular plane. The inlet plane can be between 1 mm to 4 mm medial of the acetabular plane. The acetabular cup can be implanted between about 1 mm to 4 mm below where the inner edge of the TAL would have been, and preferably about 2 mm-3 mm below.

The acetabular cup can be implanted at a position at which a rim part of the acetabular cup would have loaded the transverse acetabular ligament.

Determining the orientation of the acetabular plane can include identifying at least three points on the labrum and transverse acetabular ligament using a trackable instrument.

Determining the orientation of the acetabular plane can include observing, examining and/or otherwise assessing the labrum and/or transverse acetabular ligament.

The method can further comprise using a trackable instrument to identify a plurality of points on the interior surface of the acetabulum.

The method can further comprise capturing an image of the acetabulum including at least a part of the labrum and assessing the labrum to evaluate what surgical procedure to use, prior to determining the orientation of the acetabular plane.

According to a further aspect of the invention, there is provided computer program code executable by a data processing device to provide any of the system aspects of the invention or the method aspects of the invention. A computer program product comprising a computer readable medium and such computer program code is also provided by the invention.

According to a further aspect of the invention, there is provided an instrument for guiding the positioning of an acetabular cup implant. The instrument can comprise a mounting for attaching the instrument to a body part of a patient, a support connected to the mounting, a guide defining a longitudinal axis and an adjustment mechanism by which the angular orientation of the guide can be adjusted about at least two different axes. By allowing the guide to pivot about two degrees of freedom, the inclination and version, or anteversion, of the longitudinal axis can be altered relative to the patient's pelvis.

Hence, the instrument can be used with a further instrument, located in the guide and bearing a trial acetabular component, to allow the orientation of the guide to be adjusted based on the orientation of the trial component relative to the plane defined by the labrum and transverse acetabular ligament. In this way, the direction of the labrum/transverse acetabular ligament plane can be mechanically captured so that the guide can be used subsequently to allow an acetabular cup component to be implanted with the correct inclination and version/anteversion as captured by the guide.

Preferably the body part is a bone and preferably a bone having a substantially fixed positional relationship relative to the acetabulum. Preferably the bone is a part of the pelvis.

A part of the instrument can provide a gauge, mark or datum which can be used with markings or gradations on the further instrument to allow the depth of the acetabular implant to be planned using the trial component prior to excising the labrum and/or transverse acetabular ligament.

Preferably, the orientation of the guide can be fixed by operating a locking mechanism. This allows the guide to be slackened to allow the guide to be pivoted to align the longitudinal axis perpendicular to the labrum/TAL plane prior to fixing the guide orientation so as to capture the direction of the labrum/TAL plane.

The adjustment mechanism can include a ball and socket joint. A ball and socket joint provides a simple mechanism allowing at least two angular degrees of freedom. A ball and socket joint can also allow the guide to be rotated about its axis.

The instrument can include a further adjustment mechanism which can be operated to adjust the separation between the guide and the support. This allows the guide to be adjusted to allow the longitudinal axis to be centred on the acetabulum, without having to dismount the instrument from the patient.

The instrument can include a yet further adjustment mechanism which can be operated to adjust the height of the guide. This allows the guide to be moved closer to and further from the acetabulum increasing its ease and accuracy of use by a practitioner.

The guide can be reconfigured to accept instruments of different sizes. Preferably the guide can be reconfigured by rotating the guide about an axis of the guide.

Preferably the guide defines a channel for receiving a further instrument. The channel can be an open channel or a closed channel. An open channel can be preferred as it make it easier to engage the further instrument with the guide. The channel can be defined by two members and preferably is defined by two opposed pairs of members.

According to a further aspect of the invention, there is provided a kit of parts including an instrument according to the preceding aspect of the invention and a further instrument comprising a body having a longitudinal axis which can be engaged in the guide and bearing an acetabular component which can be used to determine the orientation of the plane defined by the labrum and transverse acetabular ligament. The further instrument can be an inserter. The acetabular component can be a trial component or a prosthetic implant component. The acetabular component can be a hemispherical component, or a planar component and is preferably a circular disk.

An embodiment of the invention will now be described, by way of example only, and with reference to the accompanying drawings, in which.

Similar items in different Figures share common reference numerals unless indicated otherwise.

Figure 1A:
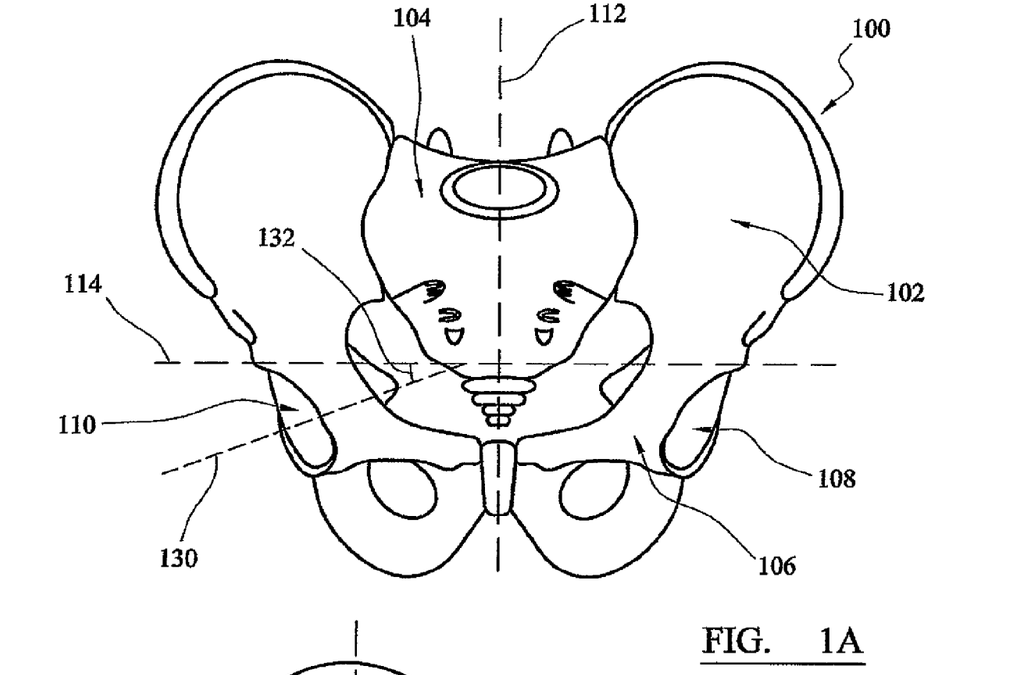
FIG. 1A shows a schematic frontal view of a pelvis.
Figure 1B:
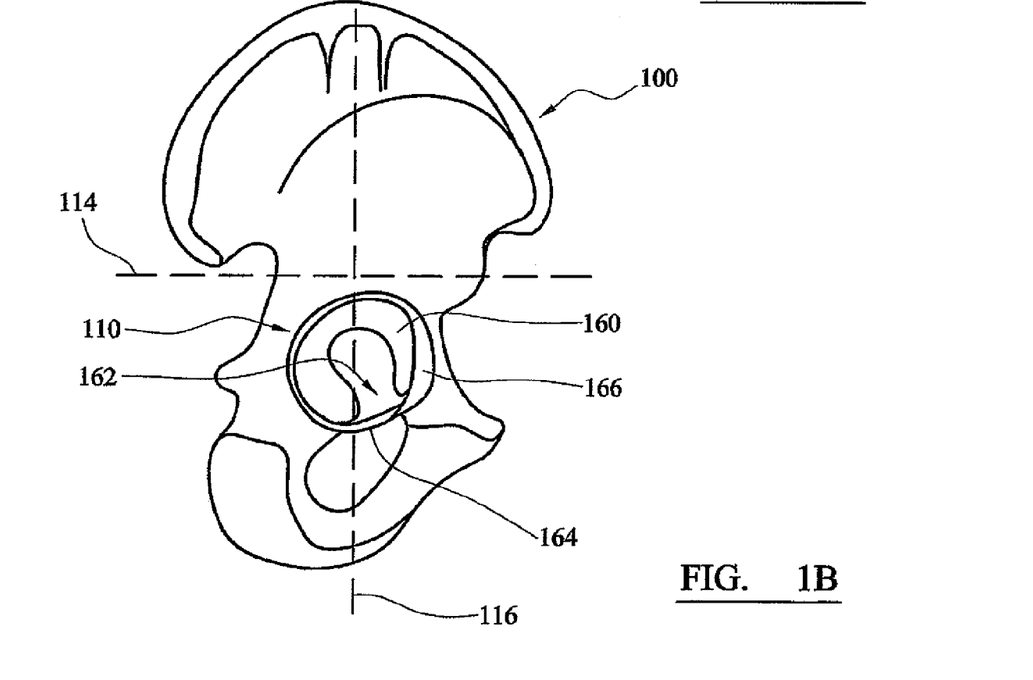
FIG. 1B shows a schematic lateral view of the pelvis shown in FIG. 1.

FIGS. 1A and 1B respectively show a frontal view and a lateral view of a human pelvis 100. The anatomy of the human pelvis is well known and includes the ilium 102, the sacrum 104, the pubis 106 and the left acetabulum 108 and right acetabulum 110. Dashed line 112 represents the local saggital or medial plane of the pelvis. Dashed line 114 represents the local transverse plane of the pelvis. Dashed line 116 represents the local frontal or coronal plane of the pelvis. The local saggital, transverse and frontal planes are mutually perpendicular and between them define a rectangular 'box' having walls parallel to the planes within which the pelvis can be considered to be contained, and as illustrated by box 120 in FIG. 2. Axes 122, 124 and 126 illustrate the 'directions' of the local cardinal planes of the pelvis, in which the local saggital plane is parallel to the plane defined by axes 122 and 126, the local transverse plane is parallel to the plane defined by axes 124 and 126 and the local frontal plane is parallel to the plane defined by axes 122 and 124.

Figures 2, 3:
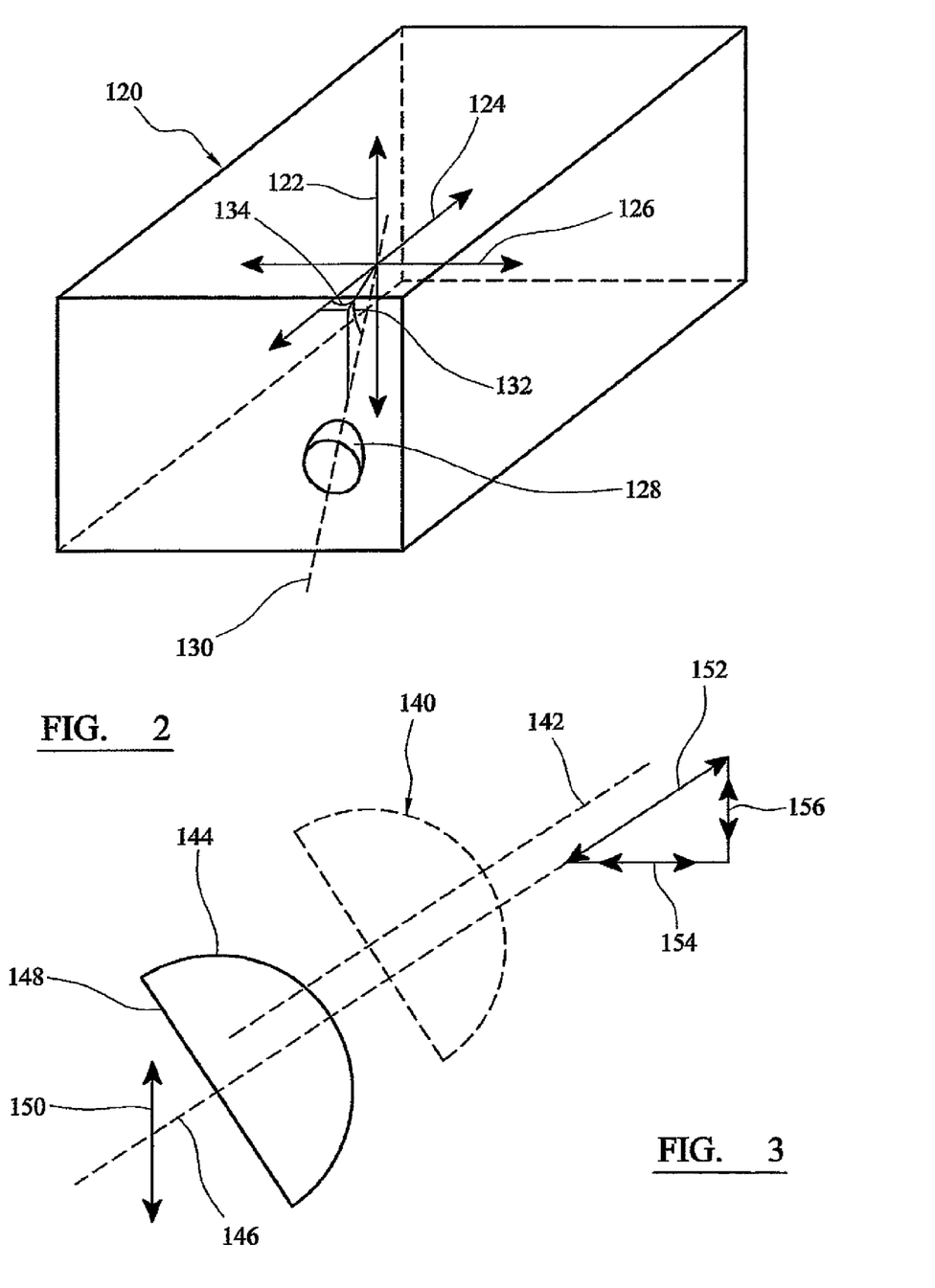
FIG. 2 shows a visual representation of the principal planes of the pelvis and the relationship between the planes of the pelvis and the orientation of an acetabular cup.
FIG. 3 shows a visual representation illustrating the relationship between the height and depth of the acetabular cup.

In the invention, the acetabulum is considered to be approximated by a hemispherical cup having a mouth or inlet plane and having an acetabular axis perpendicular to the plane of the mouth or the inlet plane, and passing through the centre of the mouth/inlet plane. This is illustrated in FIG. 2 by hemispherical cup 128 and dashed line 130 representing the acetabular axis. The orientation, i.e. the angular disposition, of the acetabulum in the pelvis can be defined by the abduction angle or inclination angle and the version angle. The abduction angle is the angle 132 subtended by the acetabular axis 130 and the transverse plane 114. The version angle is the angle 134 subtended by the acetabular axis 130 and the frontal plane 116. Hence, the orientation of the acetabulum, to which the orientation of the acetabular cup implant should be aligned, is defined by the version and abduction angles.

In order to determine how to correctly implant the acetabular cup it is also necessary to determine the correct position within the acetabulum at which to locate the acetabular cup, with the correct orientation. The position of the acetabular cup is determined by the depth within the acetabulum and the height in the cordal-cranial direction. The insertion depth of the acetabular cup in the acetabulum, is approximately along the acetabulum axis and determines the position of the fulcrum of the lever system comprising the femur and the muscles of the pelvis. The height is important in terms of defining the bio-mechanics of the hip as it determines the rotation centre of the hip joint. In FIG. 3, dashed line 140 indicates the planned implantation position of the acetabular cup having the desired height and depth. Dashed line 142 indicates the acetabular axis of the planned position which defines the correct orientation of the acetabular cup 144. Acetabular cup 144 has acetabular axis 146 and as illustrated in FIG. 3, the orientation of acetabular cup 144 is aligned with the orientation of the planned position. When aligned, the inlet plane of the acetabular cup 148 is substantially parallel with the inlet plane of the acetabulum.

In order to align the position of the acetabular cup 144 with the planned position 140, the height of the acetabular cup in the direction of arrow 150 can be varied. Also, the depth of the acetabular cup in the direction of arrow 152 can be varied. The depth is generally a translation in a direction parallel to the acetabular axis. However, unless the acetabular axis has substantially zero abduction, varying the depth of the acetabular cup 144 also changes the height of the acetabular cup as illustrated by the decomposition of the depth vector 152 into transverse 154 and height components 156. Hence, when aligning the acetabular cup 144 with the planned position 140 the effect of the depth in the acetabulum on the height of the cup should be taken into account for the most accurate alignment.

FIG. 1B also shows the lunate surface 160 of the acetabulum 110 and the acetabular notch 162. FIG. 1B also shows the transverse acetabular ligament (TAL) 164 which is the ligament which extends across the acetabular notch and connects the two ends of the facies lunata. FIG. 1B also shows the acetabular labrum (AL) 166 which is a fibro-cartilaginous extension of the bony rim of the acetabulum. The acetabular labrum 166 increases the effective depth of the acetabulum and therefore the depth of the femoral head in the acetabulum without increasing the bony coverage. Hence the range of motion of the femur is increased as the labrum can deform if engaged by the neck of the femur.

The present invention uses the TAL and AL as anatomical landmarks for determining the correct position at which to implant an acetabular cup prosthesis. It is believed that between them, the TAL and AL, rather than the bony rim of the acetabulum, define the functional inlet plane of the acetabulum. As the TAL and AL are generally unique to each patient they can be used to provide a patient specific indication of the correct position for the acetabular cup implant, rather than having to rely on other anatomical landmarks to guide the cup implantation. In general, the TAL is used as a landmark for determining the version angle, insertion depth and height of the cup and the AL is used as a landmark for determining the abduction angle.

Surgical methods for determining the correct implantation position using the TAL and AL as landmarks can be computer aided surgery (CAS) methods or non-CAS methods. CAS methods can provide the surgeon with guidance as to the correct positioning, by implementing an image guided surgery (IGS) procedure, so as to improve the accuracy of the surgical technique. Non-CAS methods can still take advantage of the present invention wherein the surgeon uses their skill and experience to determine the correct cup implant position using the TAL and AL as landmarks.

Figure 4:
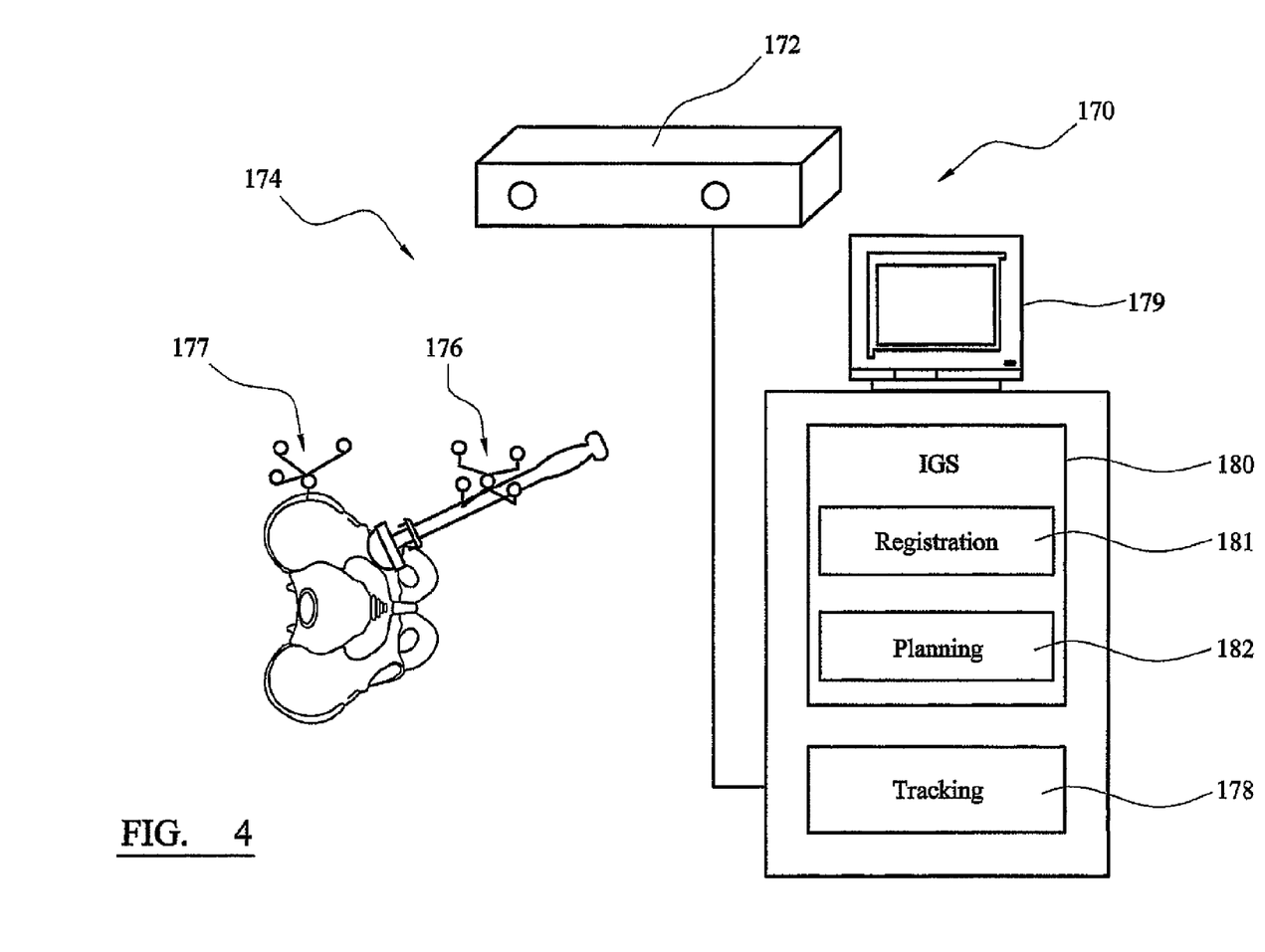
FIG. 4 shows a computer aided surgery system according to the invention.

FIG. 4 shows a CAS system 170 according to the invention. CAS system includes a tracking sub-system 172 for tracking suitably marked parts of the patient's anatomy (such as the pelvis), instruments, tools, templates, implants and other items used by the surgeon. In the illustrated embodiment, an infrared based system is used in which a pair of image capturing devices 174 capture images of star arrays 176, 177 of IR reflective spheres mounted on the item being tracked. A suitable IR based tracking system is provided under the name VectorVision by BrainLAB AG. In other embodiments, other forms of tracking technology can be used. For example wire based tracking can be used and other forms of wireless tracking can be used, such as acoustic based tracking and electromagnetic or magnetic field based tracking.

A magnetic field based tracking system can use a number of coils to generate a 3-d magnetic field distribution in an operating volume. A sensor which includes three mutually perpendicular sensor coils to determine the components of the magnetic field can be used to mark the items. Onboard electronics of the sensor wirelessly transmits a signal from the sensor coils back to the tracking system which is processed by the tracking software to determine the position and orientation in the reference frame of the CAS system of the item to which the sensor is attached.

Tracking software 178 processes the captured images to derive tracking data representing the real time position and orientation of the tracked item in a reference frame of the CAS system. CAS system 170 also includes a visual display device 179 on which visual indications of the position of tracked items, body parts of the patient, such as the pelvis, and planned positions can be displayed to the surgeon. The display device can also provide a graphical user interface by which the surgeon interacts with and operates the CAS system. The display can be a touch sensitive display so that the surgeon can enter commands and select options by touching the screen of the display device.

The CAS includes IGS software 180 which can include a module 180 to handle registration of the patient and/or images with the CAS system 18 and a module 182 to perform an IGS procedure which defines a workflow including navigated planning of the implantation position, navigated reaming of the acetabulum and navigated implantation of the acetabular cup prosthesis.

Figure 5:
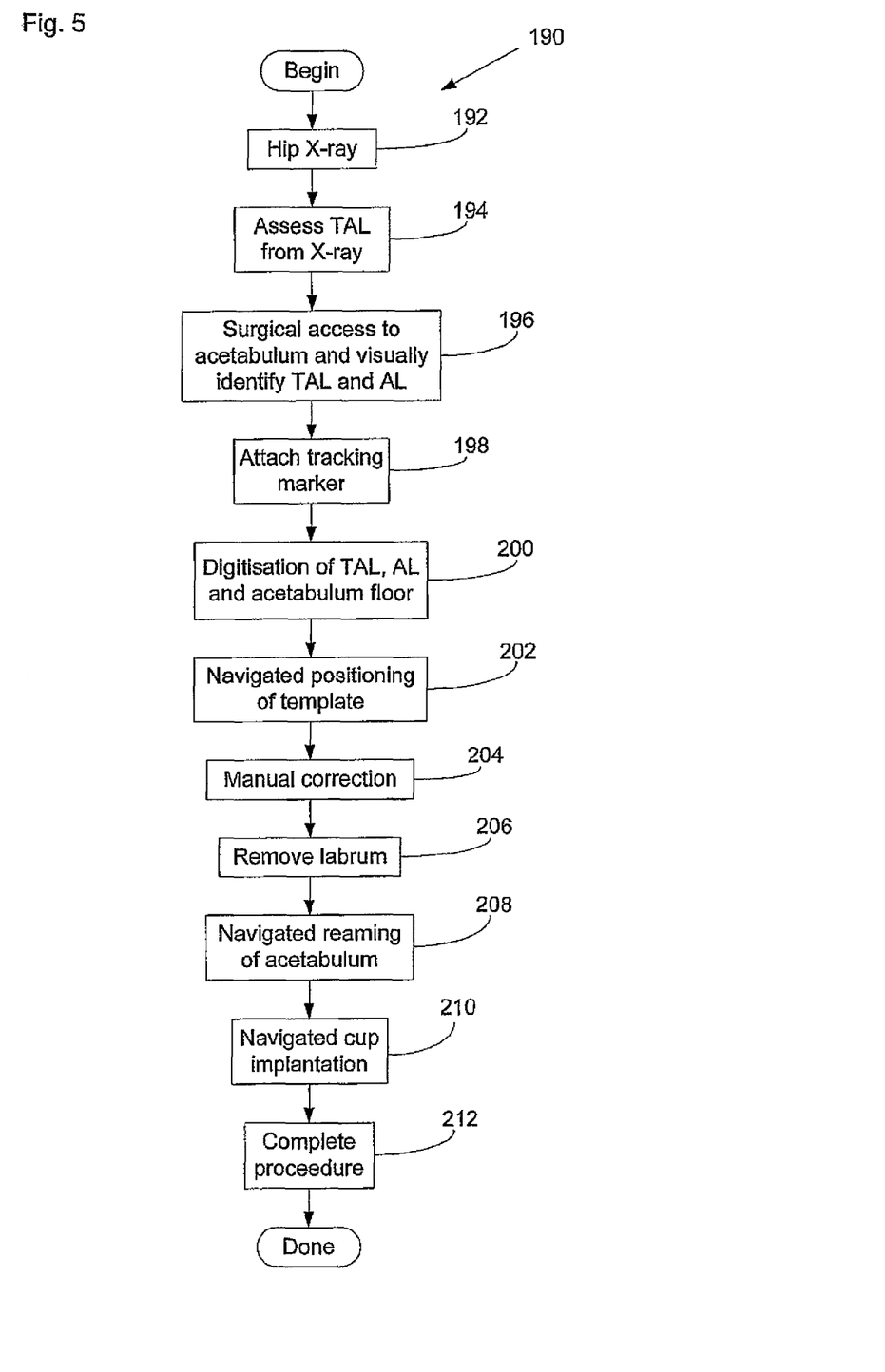
FIG. 5 shows a flow chart illustrating a surgical method according to the invention.

FIG. 5 shows a flow chart illustrating a surgical method 190 carried out by a surgeon using the CAS system 170 of FIG. 4. As mentioned previously, it is not necessary to use a CAS method and in other embodiments of the invention a non-CAS or less CAS dependent surgical method can be used instead.

Surgical method 190 begins and at a preoperative step 192, an X-ray image of the patient's pelvis is captured. Although the TAL is not visible on the X-ray image, since it is a soft tissue structure, there is a link between the appearance of the bones in the X-ray image the close vicinity of the TAL that indicates the likelihood of subsequent identification of the TAL in situ. Then at step 194 an assessment of the TAL appearance can be carried out by the surgeon based on the X-ray image in order to determine whether the procedure is suitable for the patient. It has been found that the TAL is present in over 95% of cases. A grading scheme has been developed for the assessment of the TAL. A TAL can be classified as type 1 if the TAL is intact and clearly visible. A TAL can be classified as type 2 if the TAL is overgrown by soft tissue but intact and would be visible after clearing the soft tissue. A TAL can be classified as type 3, if the TAL is overgrown by osteophyte but intact and would be clearly visible after removing the osteophyte. A TAL can be classified as type 4 if the TAL is absent or incomplete. If the visual assessment of the TAL results in the TAL being classified as type 4, then the surgeon may decide that the procedure of the present invention is not suitable and may select a different surgical procedure for determining the cup position.

Steps 192 and 194 are optional and may be omitted in some embodiments.

At step 196, the surgeon gains access to the acetabulum and visually identifies the TAL and remnants of the AL. Then at step 198, the surgeon attaches a tracking marker to the pelvis so that the position of the pelvis can be registered with the CAS system and its position tracked. Registration involves registering the position of the actual body part in the reference frame of the CAS system. Then at step 200, using a trackable pointer, the surgeon identifies at least two points on the TAL. In particular, the positions of the insertion and origin points of the TAL are identified by the surgeon using the trackable pointer and the CAS system determines and stores the positions. The insertion and origin points define the distance. The origin and insertion points are the end points of the TAL. The origin is located closer to the mid line of the human body, that is toward the acetabular rim end on the pubic bone. Insertion is the point further away from the mid line of the human body, that is toward the acetabular rim end on the illium bone.

The surgeon also uses the trackable pointer to identify at least one point, and typically a plurality of points, on the remnants of the AL or where, in the surgeon's judgement, the AL would have been if there is little or none of the AL remaining. Points are collected on the labrum and preferably the posterior and superior part, but other points can also be used. The surgeon then uses the trackable pointer to identify a plurality of points on the inner surface of the acetabulum so as to digitise the shape of the inner surface of the acetabulum.

As will be described in greater detail below, the CAS system determines a template acetabular cup that best fits the size of the acetabulum and also determines the orientation of the inlet plane of the acetabulum from the TAL and AL positions and the acetabular axis perpendicular to that plane. The best fitting template acetabular cup is trackable and the position of the cup is tracked by the CAS system and a visual indication of its orientation and position and of the orientation of the acetabulum inlet plane are displayed on the visual display of the CAS system. At step 202, the surgeon manipulates the template in the acetabulum and uses the visual indication of the orientation of the acetabulum to align the orientation of the template.

The surgeon also manipulates the template to alter the height and the depth of the template.

Figure 7A:
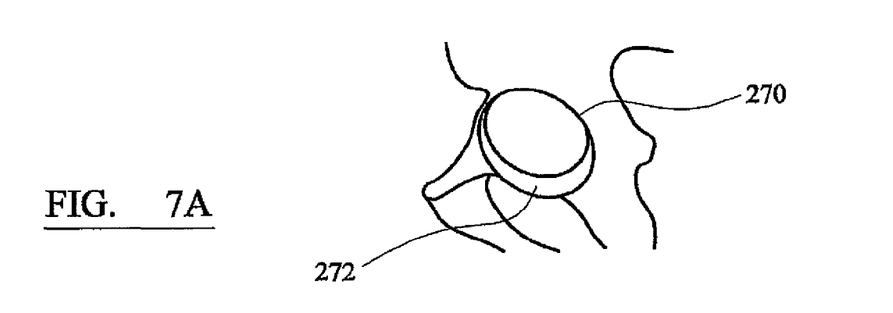
FIGS. 7A to 7E show acetabular cup positions in the acetabulum illustrating a too high cup position, a too deep cup position, a correct cup position, a cup anterverted position and a cup retroverted position respectively.

The height of the template is determined by ensuring that the template cup slightly distracts or loads the TAL, rather than the TAL simply being tangential or too superior to the TAL. For example, FIG. 7A illustrates the scenario in which the template cup 270 is too high as the TAL 272 is not loaded.

Figure 7B:
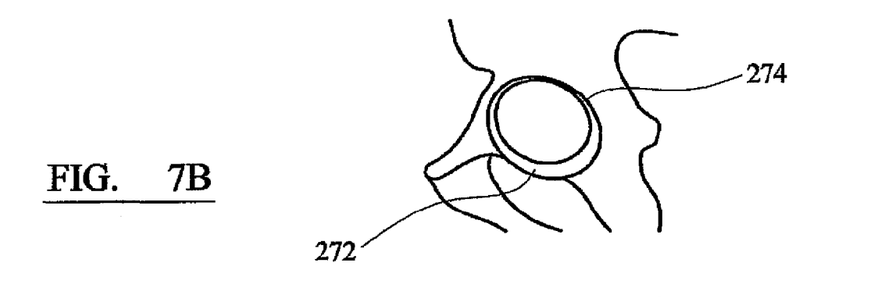

The depth of the template is determined by ensuring that the template lies just deep, i.e. medial to, the rim formed by the TAL and AL. In particular it has been found that positioning the template at a depth such that the inlet plane of the template is approximately 3-4 mm below the rim produces good results. For example, FIG. 7B illustrates the scenario in which the template cup is too deep as the template cup inlet plane 274 is too far below the TAL 272.

When the surgeon has determined that the template cup is in the right orientation and at the correct position in the acetabulum, then the CAS system stores the planned position for the actual prosthetic cup. At step 204, the surgeon can review the planned position, and if necessary enter commands to manual adjust or change the planned position. Then at step 206 surgery progresses and the surgeon excises the labrum and prepares the acetabulum for reaming. Then at step 208, the surgeon reams the acetabulum using a trackable reamer. The CAS system determines the correct orientation and final position of the reamer and displays a real time visual indication of the reamer's current position and correct end position to enable the surgeon to accurately navigate the reamer so as to ream the acetabulum correctly to receive the acetabular cup implant.

Then at step 210 the surgeon obtains a trackable acetabular cup prosthesis and uses the CAS system to navigate the acetabular cup prosthesis to its correct orientation and position in the reamed acetabulum and implants the acetabular cup prosthesis at the planned position. The surgeon then continues with the remaining steps of the hip replacement procedure at step 220 until the procedure is complete.

Figure 6:
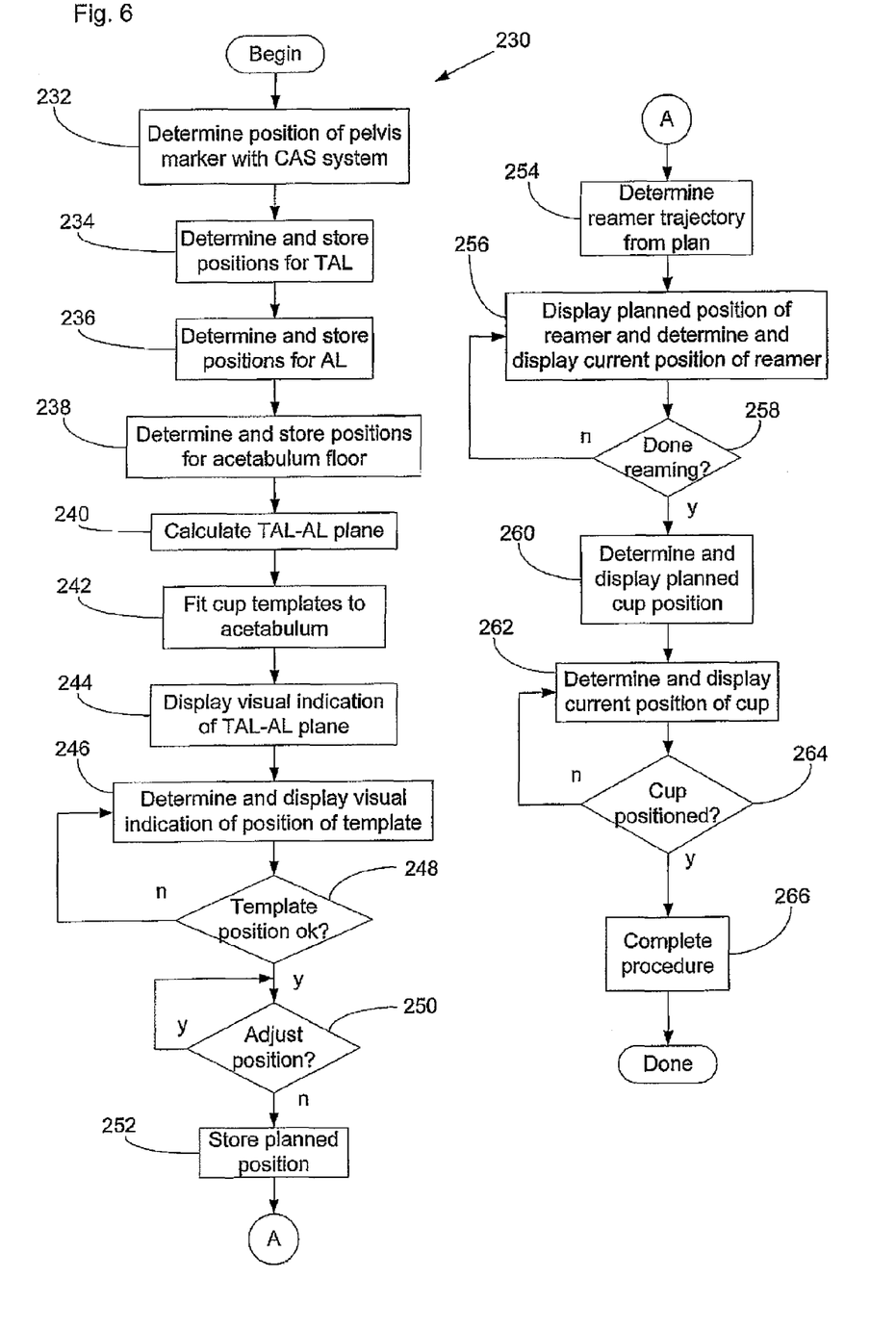
FIG. 6 shows a process flow chart for a computer aided surgery method according to the invention.

FIG. 6 shows a process flow chart illustrating operations carried out by the CAS system under control of software to provide a CAS method 230 according to the invention. As mentioned previously CAS system 170 includes an IGS module and a tracking module 178. The tracking module receives input from the tracking system and provides data to the IGS module indicating the real time, current orientation and position of various trackable items in the reference frame of the CAS system. The IGS system defines a workflow setting out a surgical procedure to be followed by the surgeon and during which the CAS system provides visual indications of the positions of the tracked items and planned positions so that the displayed images guide the surgeon so as to navigate the instruments and implants to the correct position and orientation.

The surgeon initiates the CAS method 230 and at step 232, data is received from the tracking module which indicates the position and orientation in the CAS frame of reference of the marker attached to the pelvis. The marker can either be attached at a predetermined position to the pelvis or the surgeon can identify to the CAS system where on the pelvis the marker has been attached. The positions of the acetabular landmarks (TAL and labrum points) can then be recorded in the coordinate system of the pelvic bone marker. Further, the tracking system can continuously track the pelvic marker so that the position of the acetabular landmarks is maintained if the patient's pelvis moves during surgery.

Then at step 234, the planning module receives data from the tracking system representing the position in the reference frame of the tracking system of the points on the TAL obtained by tracking the trackable pointer used by the surgeon, and stores the TAL position data. Then at step 236, the planning module receives data from the tracking system representing the position in the reference frame of the tracking system of the points on the AL obtained by tracking the trackable pointer used by the surgeon, and stores the AL position data. Then at step 238, the planning module receives data from the tracking system representing the position in the reference frame of the tracking system of the points on the inner surface of the acetabulum obtained by tracking the trackable pointer used by the surgeon, and stores the acetabular shape position data.

Then at step 240, using the TAL and AL position data, the plane including the TAL and AL positions is calculated. Then at step 242, a hemisphere is fitted to the shape of the acetabulum, in which the inlet plane or mouth of the hemisphere is parallel to the TAL-AL plane and the diameter is determined by the width and depth of the acetabulum from the acetabulum shape position data. An acetabulum axis can then be defined as the axis passing through the centre of the hemisphere, which will be perpendicular to the TAL-AL plane. The CAS system then compares the fitted hemisphere with the size of a number of acetabular cup templates to determine the template best matching the shape of the acetabulum. The best matching template is displayed or otherwise identified to the surgeon who then uses the best matching template in order to complete planning the implant position.

At step 244 a visual indication of the calculated position of the TAL-AL plane is displayed to help guide the surgeon. The tracking module supplies data representing the position and orientation of the tracked template and at step 246, the planning module displays the current position and orientation of the trackable template. As both the TAL-AL plane and the position and orientation of the template are displayed, the surgeon can use the displayed information to help manipulate and position the template so that its acetabular axis is parallel with the acetabulum axis, or equivalently so that the inlet plane of the template is parallel with the inlet plane of the acetabulum. At step 248, the CAS system checks whether the template position has been finalised and if not process flow returns to step 246 and processing loops.

Figure 7C:
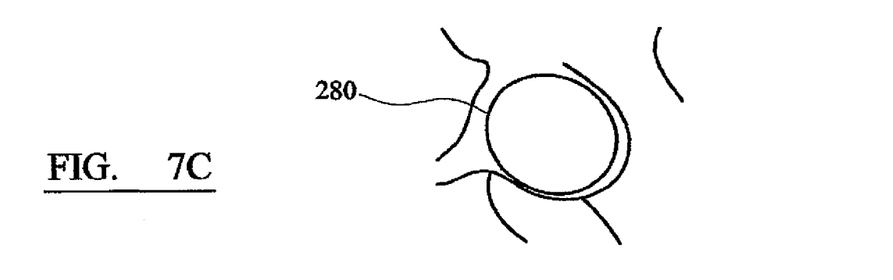
Figures 7D, 7E:
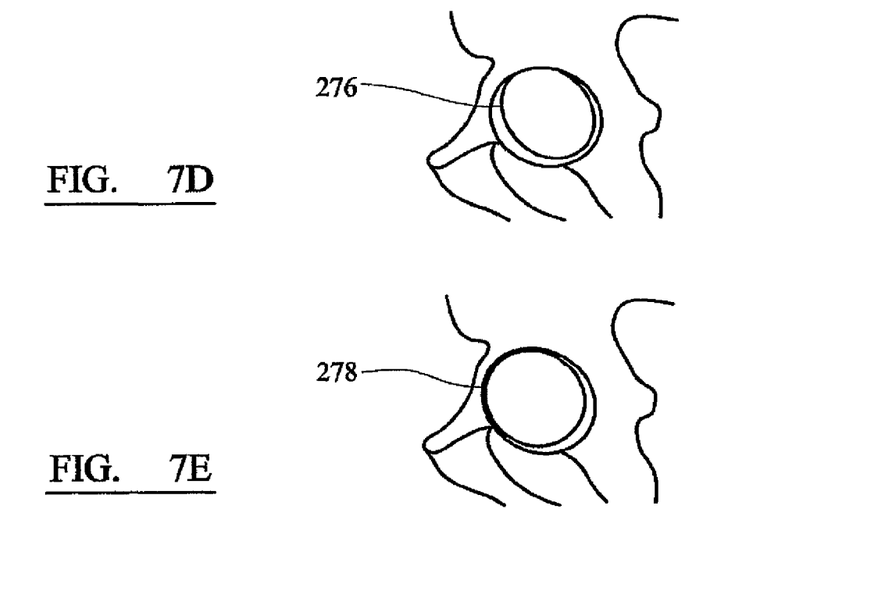

When the surgeon enters a command to indicate that the template is at the correct position, then process flow proceeds to step 250. The CAS system provides the option to enter commands to manually adjust the version, abduction, height or depth. Although the template cup inlet plane should be parallel to the calculated TAL-AL plane, visual inspection by the surgeon may establish that the template cup orientation is not optimum for the specific pelvis. For example, FIG. 7D illustrates a scenario in which the template cup 276 orientation is anteverted and FIG. 7E illustrates a scenario in which the template cup 278 orientation is retroverted. The surgeon can enter commands to change the version angle until he is happy with the alignment of the template cup. In particular, the version angle should be such as to make the inlet plane of the cup parallel with the TAL.

The surgeon can also enter commands to manually change the abduction angle until he considers the inlet plane of the template cup to be parallel with the AL or remnants thereof. The surgeon can also enter commands to adjust the height of the cup. The height of the cup should be such as to just load the TAL. A registered visual representation of the acetabulum and TAL can also be displayed to the surgeon derived from previously captured images, such as x-ray or CT scan images, or from generic models. The surgeon can also enter commands to alter the depth of the template cup. The inlet plane of the template cup should be about 2-3 mm, ∀1 mm, below the inner edge of the TAL. For example, FIG. 7B illustrates the scenario in which the template cup 274 is too deep. FIG. 7C illustrates the scenario in which the template cup 280 position and orientation are both correct.

Manual adjustment of the cup position 250 can continue until the surgeon enters a command indicating that this is the final planned cup position and then processing proceeds to step 252 at which the planned cup position is stored. Then at step 254, using data representing the planned cup position, the correct trajectory, i.e. the orientation of the reamer and the depth or reaming along that direction, is determined. As mentioned previously, the depth of reaming should be such as to locate the acetabular cup implant at both the correct depth and height. At step 256 a visual indication of the planned trajectory of the reamer is displayed together with the real time, current position of the reamer, derived from reamer tracking data provided from the tracking module. This visual information helps to guide the surgeon so that he can navigate the reamer to ream a cavity having the correct depth, height and orientation. If at step 258, it is determined that reaming has not been completed, then process flow returns to step 256 and processing continues to loop.

When reaming has been completed, the planned position and orientation of the acetabular cup implant is displayed at step 260. Then at step 262 the real time, current position of the acetabular cup prosthesis, derived from prosthesis tracking data provided from the tracking module, is displayed together with the planned position. This visual information helps to guide the surgeon so that he can navigate the prosthesis to the implantation position having the correct depth, height and orientation. The reamed cavity should help to ensure the correct height and depth and this visual information particularly assists in ensuring that the implanted cup has the correct orientation as the AL is no longer available for visual alignment. If at step 264, it is determined that cup positioning has not been completed, then process flow returns to step 262 and processing continues to loop. When the cup has been correctly positioned, then this part of the CAS method can end and other CAS processes can be used in completing the surgical procedure if required.

As mentioned above, it is not necessary to use a CAS system in order to enjoy the benefits of the present invention. In a non-CAS method, a suitable instrument can be attached to the pelvis and aligned with the TAL-AL plane prior to excising the AL and then a cup template or cup prosthesis can be aligned with the plane defined by the instrument. The cup template or cup prosthesis depth and height can be determined by visual inspection of the position of the cup template or cup prosthesis relative to the TAL using the criteria described above.

The present invention has a large number of advantages over prior approaches to acetabular cup positioning.

The approach of the present invention is believed to more accurately reproduce the patient's original mobility as it is based on recognising that the TAL-AL plane defines the functional plane of the hip joint more than the bony rim of the acetabulum.

Further, the approach of the present invention is patient specific and can be optimised for each patient.

The approach is applicable to the majority of patients as the TAL ligament has been found to be sufficiently identifiable in over 95% of cases.

The approach also provides significant benefits when provided as CAS procedure. There is no need to identify the cardinal planes of the pelvis as alignment is achieved relative to the TAL and AL anatomical landmarks. The patient can be positioned in any position in which access to the TAL and AL are available, rather than having to use a special position in order to allow access to landmarks allowing the cardinal planes of the pelvis to be identified. There is no need to re-align the pelvis with the body if the patients pelvis moves during surgery, as is the case in approaches based on determining the abduction and version relative to global planes.

Figure 8:
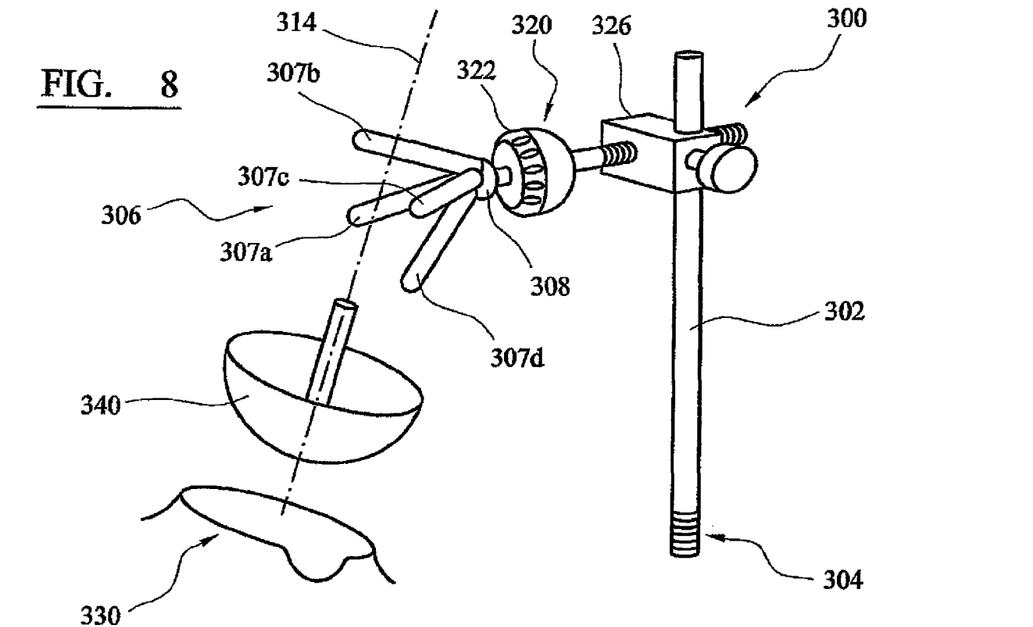
FIG. 8 shows a schematic illustration of an instrument for use in guiding the placement of an acetabular cup implant.
Figure 9:
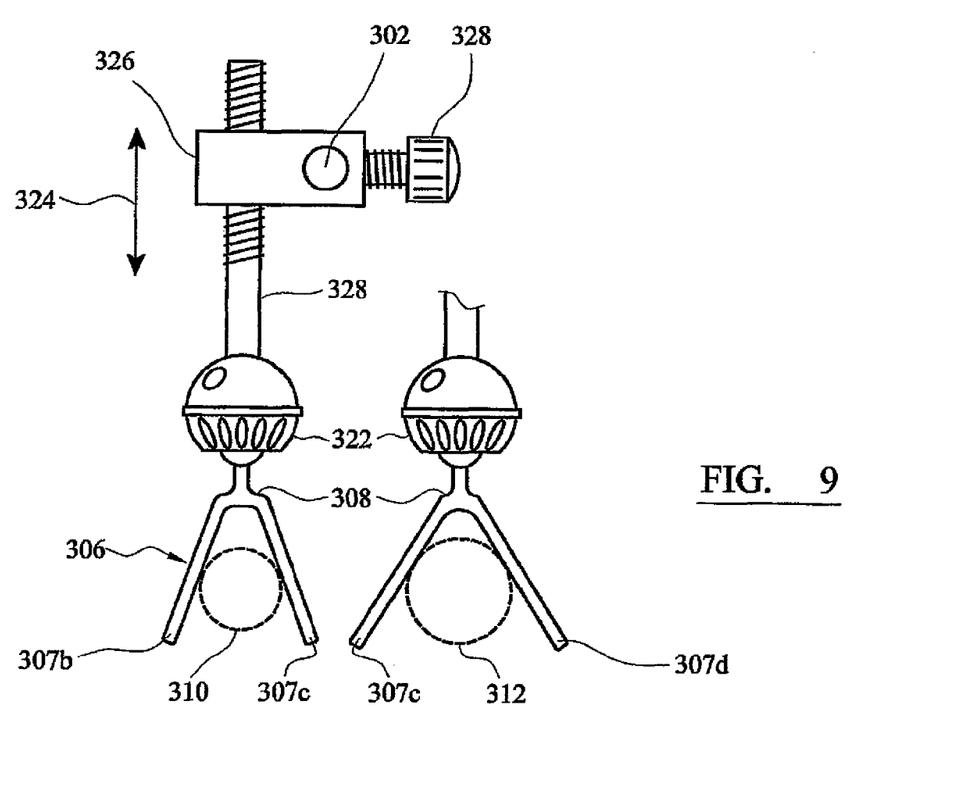
FIG. 9 shows a part of the instrument shown in FIG. 8.

With reference to FIGS. 8 and 9 there are shown a schematic perspective view of an instrument 300 according to the invention and a plan view of adjustment and guide parts respectively. As shown in FIG. 8, the instrument 300 includes a circular rod 302 having a bone screw 304 at a distal end thereof. Rod 302 provides a support element and bone screw 304 provides a mounting by which the support 302 can be attached to a patient's body part in use. It will be appreciated that different types of mounting mechanisms can be used. For example, a clamp type mechanism can be used to attach the support to a patient's body part. All that is required is that the mount allows the support to be releasably attached to the patient's bone, e.g. to a part of the pelvis, with sufficient strength as to allow the positioning of instruments to be guided in use, as will be described in greater detail below.

Instrument 300 also includes a guide element 306 which includes four splayed arms 307a, 307b, 307c, 307d attached to a central mounting or hub 308. As best illustrated in FIG. 9, the angle between opposed pairs of arms is greater in a first direction compared to a second perpendicular direction. Hence, by rotating the guide through 90E, the guide can accept different diameter instruments 310 and 312 as illustrated in FIG. 9. As illustrated in FIG. 8, the upper and lower pairs of arms define a longitudinal axis 314 of the guide and can accept an instrument within an open channel defined by the splayed arms of the guide so as to orient the instrument along the longitudinal axis defined by the arms of the guide.

Instrument 300 also includes various adjustment mechanisms by which the angular orientation and position of the guide 306 can be adjusted or changed relative to the pelvis of the patient. The instrument includes a first adjustment mechanism 320 in the form of a lockable spherical joint, such as a ball and socket joint. This adjustment mechanism allows the angular orientation of the guide to be varied about two mutually perpendicular axes providing two rotational or pivotal degrees of freedom. A third rotational degree of freedom is also provided by the ball and socket joint which allows the guide to be rotated about its own longitudinal axis (rather than guide axis 314) so that the guide can be used in the two different configurations illustrated in FIG. 9. The first adjustment mechanism 320 includes an annular, knurled threaded member which can be slackened to allow the angular orientation of the guide to be adjusted and then tightened to fix the angular orientation of the guide.

The instrument includes a second adjustment mechanism by which the separation between the guide 306 and the support 302 can be varied as illustrated by double headed arrow 324. The second adjustment mechanism is in the form of a block 326 having a threaded circular passage therethrough which receives the threaded shank of a rod 328 connected to a rear side of the socket part of the first adjustment mechanism 320. By rotating rod 328, the action of the screw thread in block 326 causes the guide to be translated away from or toward support 302 thereby allowing the distance between the support and guide in a generally transverse direction to be adjusted. It will be appreciated that other adjustment mechanisms can be used to allow the separation between the guide and support 302 to be adjusted.

Block 326 also provides an element of a third adjustment mechanism by which the height of the guide 306 can be adjusted. Block 326 includes a circular channel, substantially perpendicular to the threaded channel, and which receives the rod of the support 302. A threaded bolt with a knurled head 328 can be operated to clamp against the rod 302 so that the height of the guide relative to the patient's body can be adjusted by slackening bolt 328 and sliding block 326 along rod 302 and tightening bolt 328 to clamp the guide at the appropriate height.

The instrument 300 can be made of any suitable biocompatible material, such as a metal or alloy, such as, for example, surgical grade stainless steel.

FIG. 8 also shows a schematic representation 330 of the acetabular cup, including the labrum and transverse acetabular ligament.

In use, the instrument is attached to the patient's pelvis using the mounting 304 and the height and separation of the guide are adjusted until the guide 306 is in an initial working position. The lock 322 of the spherical joint is slackened to allow the angular position of the guide 306 to be adjusted. Then a further instrument 340, such as an inserter or a reamer with a trial acetabular component, which may be a hemispherical component or cup or simply a circular disc having the diameter of an intended cup implant, is engaged in the channel of the guide so that the body of the instrument is received in the jaws and guided along the longitudinal axis 314 of the guide. The acetabular trial component, instrument and guide can then be manipulated by the practitioner so that the plane of the acetabular trial component is substantially parallel to the plane defined by the acetabular labrum and the transverse acetabular ligament. This effectively includes varying the inclination and/or version or anteversion of the trial component, defined by the direction of axis 314, relative to the patient's pelvis.

Once the orientation of the guide is correct, such that axis 314 is substantially perpendicular to the plane defined by the acetabular labrum and the transverse acetabular ligament, then the spherical joint is locked to fix the guide in place. As will be appreciated, aligning the trial component with the plane of the acetabular cup may be an iterative procedure requiring repeated adjustment of any and all of the angular orientation of the guide and/or its height and/or its separation from the support 302.

Additionally, the planned depth of the implant can be determined by translating the further instrument and acetabular trial component along the axis 314 into the acetabulum and using marking or gradations on the body of the further instrument to gauge the depth of the implant using a datum on the guide, such as hub part 308.

Once the guide orientation has been fixed, then the surgeon can remove the labrum, transverse acetabular ligament and ream the acetabular cavity. Then a full trial cup can be inserted into the reamed acetabulum using an inserter instrument engaged within the jaws of the guide instrument so as to be oriented along axis 314. The inserter instrument can again have gradations or other marks along its body to determine the depth of insertion of the trial into the reamed acetabular cavity. The depth of the trial implant can be determined by reading the marking on the instrument relative to the same datum provided by the central hub 308 of the guide.

Then, the implant itself can be inserted using the same or a similar instrument having similar markings so that the depth of insertion corresponds to that determined for the trial implant and also such that the angular orientation of the acetabular cup implant corresponds to that determined initially.

In other embodiments, the instrument 300 can be used in connection with the CAS system described previously and a trackable marker can be attached to the guide to allow the position and/or orientation of the guide to be determined and displayed. The acetabular cup trial or implant and/or further instrument bearing them can additionally or alternatively be provided with a trackable marker so that the position and/or orientation of the further instrument and/or acetabular trial or implant can be determined and displayed as part of an IGS procedure.

The above described flow charts are by way of illustration only and the invention need not necessarily include all the illustrated steps, some of the steps may be combined into a single step, others of the steps may be decomposed into sub-steps and further steps may be added or have not been described as being apparent to a person of ordinary skill in the art. Various modifications and adaptations of the present invention will be apparent to a person of ordinary skill in the art in view of the above description of the principles of the invention.

The invention claimed is:

1. A method for guiding positioning of an acetabular cup in a pelvis of a patient, comprising the steps of:
   displaying, on a display device, a visual representation of an orientation of an acetabular plane including an acetabular labrum and a transverse acetabular ligament of the pelvis;
   during the step of displaying, tracking, in a computer aided surgery system, a trackable instrument fixedly attached to the pelvis; and
   implanting the acetabular cup in an acetabulum of the pelvis with an inlet plane of the acetabular cup oriented substantially parallel to the acetabular plane.

2. The method of claim 1, further comprising the step of determining an acetabular cup template that best matches a shape of the acetabulum.

3. The method of claim 2, further comprising tracking a position of an acetabular cup template with the computer aided surgery system as the template is moved relative to the acetabulum.

4. The method of claim 1, wherein the acetabular cup is implanted at a position at which the inlet plane is located medial of the acetabular plane.

5. The method of claim 4, wherein the inlet plane is between 1 mm and 4 mm medial of the acetabular plane.

6. The method of claim 1, wherein the acetabular cup is implanted at a position at which a rim part of the acetabular cup loads the transverse acetabular ligament.

7. The method of claim 1, further comprising the step of handling a trackable pointer; and wherein determining the orientation of the acetabular plane comprises the step of contacting at least two points on the transverse acetabular ligament with the trackable pointer.

8. The method of claim 1, further comprising the steps of capturing an image of the acetabulum including at least a part of the labrum and assessing the labrum to evaluate what surgical procedure to use, prior to determining the orientation of the acetabular plane.

* * * * *